(12) United States Patent
Atzinger et al.

(10) Patent No.: US 8,136,989 B2
(45) Date of Patent: Mar. 20, 2012

(54) X-RAY DETECTOR

(75) Inventors: Michael Atzinger, Seybothenreuth (DE); Ingo Hollenborg, Schwerte (DE)

(73) Assignee: Siemens Aktiengesellschaft, Munich (DE)

( * ) Notice: Subject to any disclaimer, the term of this patent is extended or adjusted under 35 U.S.C. 154(b) by 768 days.

(21) Appl. No.: 12/284,239

(22) Filed: Sep. 19, 2008

(65) Prior Publication Data

US 2011/0170660 A1 Jul. 14, 2011

(30) Foreign Application Priority Data

Sep. 24, 2007 (DE) .......................... 10 2007 045 521

(51) Int. Cl.
*H01J 31/49* (2006.01)
*H05G 1/02* (2006.01)
*H05G 1/64* (2006.01)

(52) U.S. Cl. .......................... 378/189; 378/98.8; 378/204
(58) Field of Classification Search .................... 378/19, 378/98.8, 189–192, 204, 210; 250/370.07–370.09; 187/211, 269; 280/6.156; 606/19; 901/2, 901/11, 14, 19–26, 50
See application file for complete search history.

(56) References Cited

U.S. PATENT DOCUMENTS

| 4,894,855 | A | * | 1/1990 | Kresse | 378/196 |
| 5,835,558 | A | * | 11/1998 | Maschke | 378/198 |
| 6,200,024 | B1 | * | 3/2001 | Negrelli | 378/197 |
| 6,435,715 | B1 | * | 8/2002 | Betz et al. | 378/197 |
| 2003/0091150 | A1 | * | 5/2003 | Barber et al. | 378/189 |
| 2007/0079443 | A1 | | 4/2007 | Hoth et al. | |

FOREIGN PATENT DOCUMENTS

| CN | 1947661 A | 4/2007 |
| DE | 88 01 775.3 A1 | 3/1988 |
| DE | 196 40 048 A1 | 4/2008 |
| JP | 10108860 A | 4/1998 |

OTHER PUBLICATIONS

German Office Action dated Jun. 16, 2008 with English translation.
Chinese Office Action dated Sep. 26, 2011 for corresponding Chinese Patent Application No. 200810173764.5 with English translation.

* cited by examiner

*Primary Examiner* — Anastasia Midkiff
(74) *Attorney, Agent, or Firm* — Lempin Summerfield Katz LLC

(57) ABSTRACT

An X-ray detector is provided. The X-ray detector is a grid wall device, having a radiation detector that is movable vertically by way of a displacement mechanism. The displacement mechanism is a scissor-type arm or an articulated arm having at least two arms hinged to one another. At least one drive device is provided for the purpose of moving the scissor-type arm or an articulated arm.

18 Claims, 2 Drawing Sheets

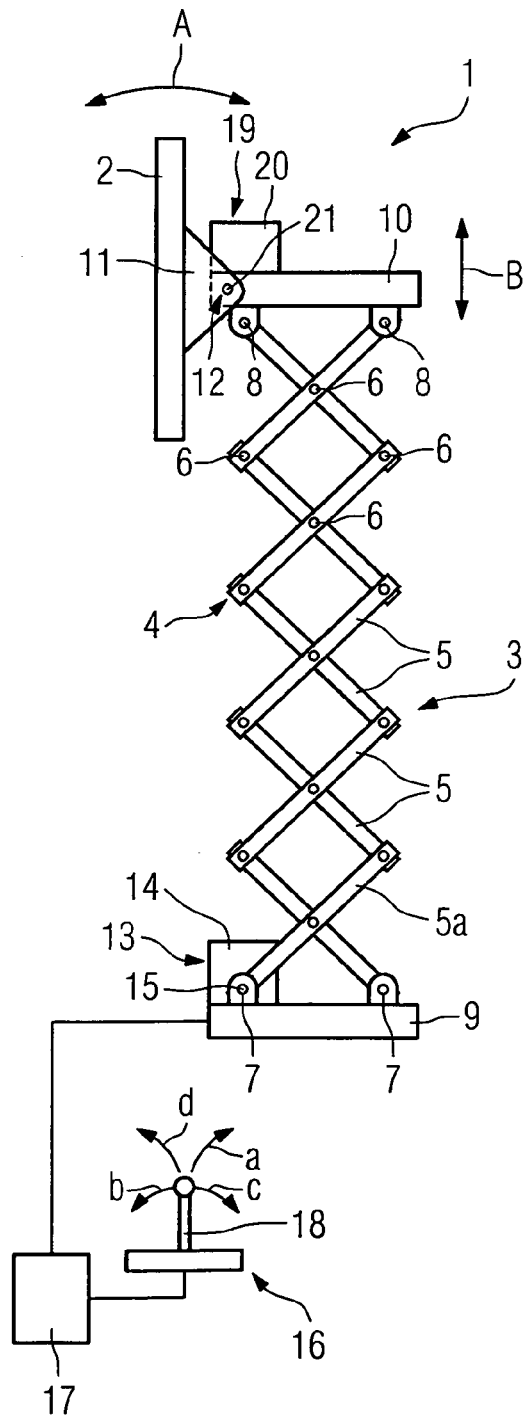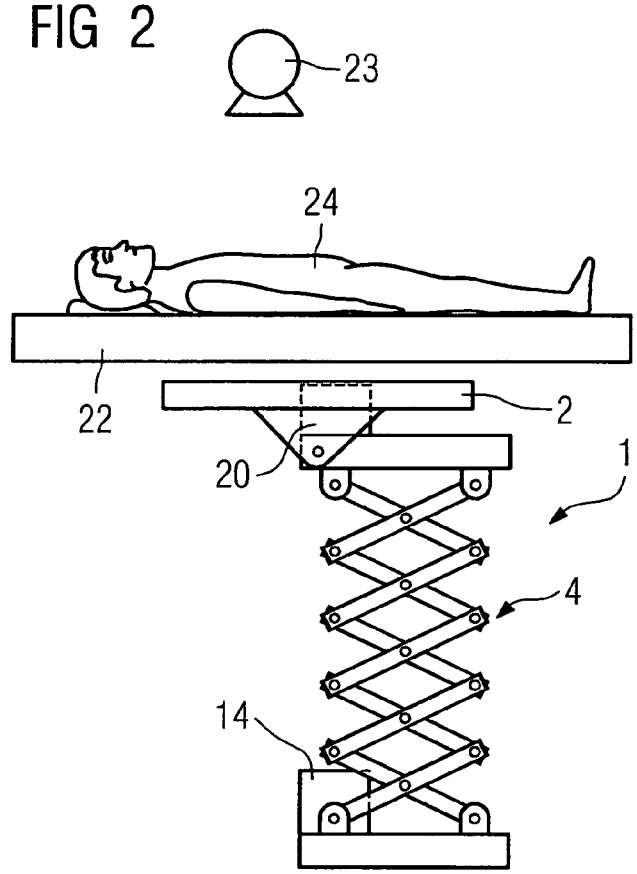

X-RAY DETECTOR

The present patent document claims the benefit of the filing date of DE 10 2007 045 521.8, filed Sep. 24, 2007.

BACKGROUND

The present embodiments relate to an X-ray detector. More specifically, the present embodiments relate to a grid wall device having a radiation detector that is movable vertically by way of a displacement mechanism.

A X-ray detector may be a grid wall device used for taking horizontal images, for example, thorax images. In this case a patient stands in front of the X-ray detector. The actual radiation detector, which detects the radiation, is positioned behind the region of the body that is to be imaged. The X-ray source is situated in front of the patient. In order to be able to take images of different regions of the body, the X-ray source and the radiation detector may be displaced vertically. The X-ray source vertically displaceable via a ceiling-mounted displacement mechanism (stand) and the radiation detector of the grid wall device has a displacement mechanism. The grid wall device is typically disposed on the floor. The radiation detector is guided on long guide rails. To facilitate movement of the radiation detector, chain drives and counterweights are provided, which are integrated in a enclosure of correspondingly large area in order to avoid injury during movement of the detector. In addition to the laborious manual detector movement, the mechanical design of X-ray detectors in the form of grid wall devices is complicated.

SUMMARY AND DESCRIPTION

The present embodiments may obviate one or more of the drawbacks or limitations inherent in the related art. For example, in one embodiment, an X-ray detector has a simple design and allows easy displacement of the radiation detector.

In one embodiment, an X-ray detector may be a grid wall device having a displacement mechanism that is a scissor-type arm or an articulated arm having at least two arms hinged to one another. At least one drive device may automatically move the scissor-type arm or articulated arm.

The X-ray detector may include a scissor-type arm or an articulated arm including at least two arms, both of which can be displaced automatically. The at least two arms are arranged such that they allow a vertical movement of the radiation detector that is movably coupled to the at least two arms. The grid wall device has a simple design because of the automatic drive and the simple design of the scissor-type arm and the articulated arm. Complex guide mechanisms, counterweights, and chain drives are unnecessary. The automatic movement relieves the load on the user and provides precise via the drive. A suitable control and operating device is used for control. For example, a simple joystick is provided for operator control, or alternatively two keys, one for controlling the upward movement and the other the downward movement. The grid wall device has a substantially simpler design because it is significantly reduced in terms of overall weight and transport size, and which is considerably easier to handle.

The drive device includes a drive motor, although other drive devices of a hydraulic or pneumatic type are also conceivable.

The drive device, for example, the drive motor, engages directly on or in a swivel joint of the scissor-type arm or articulated arm, such as a bottommost swivel joint adjacent to the floor-side mounting of the scissor-type arm or articulated arm. The scissor-type arm or articulated arm is mounted on the floor side using a suitable bearing plate. The drive device, for example, the drive motor, is disposed in this area in such a way that it can directly engage the respective arm in the area of the bottommost swivel joint. This enables a compact, stable design, which allows a reliable arm movement.

With a scissor-type arm, the two scissor halves may be coupled movably to one another via the corresponding articulated shafts, such that the entire scissor-type mechanism is automatically opened or closed when a scissor-type strut or a swivel joint is moved. Accordingly, in the case of an articulated arm, both arms are movably coupled via a mechanical coupling. When the lower arm is moved about a floor-side rotatable mounting, the movement coupling enables the second arm, which is coupled to the first via a swivel joint, to move in corresponding fashion by the same adjustment angle around this swivel joint connecting the two arms. Moving only the lower articulated arm or the bottommost swivel joint causes both arms of the articulated arm to be swiveled and either moved apart or brought together.

The movement coupling between the two articulated arms may be a chain or belt drive. The movement coupling, such as a chain or belt drive, is disposed in the interior of the lower arm and extends between the lower swivel joint and the swivel joint connecting both arms. Disposed on the respective articulated shaft is, for example, a sprocket wheel or a belt pulley around which the chain or belt is guided. If the lower articulated shaft is now turned via the drive motor, for example, the upper articulated shaft that connects both arms is automatically rotated by way of this movement coupling. The shaft is connected to the upper arm, with the result that the latter is displaced accordingly. The movement coupling may be configured such that both arms are moved by the same swiveling angle. In this way a uniform movement of both arms may be achieved.

In order not to change the set relative position of the radiation detector during a vertical movement thereof, the radiation detector is arranged on the scissor-type arm or articulated arm in such a way that the radiation detector does not change position relative to the vertical during a movement of the scissor-type arm or articulated arm. The radiation detector may be disposed in a vertical position. In order to avoid the radiation detector being moved out of this position during the vertical movement of the scissor-type or articulated arm and into a tilt position from which it would then have to moved back into the vertical position, a corresponding arrangement of the radiation detector is provided which ensures that the radiation detector remains in the vertical position independently of the scissor-type or articulated arm movement.

In one embodiment, the X-ray device includes a scissor-type arm. The radiation detector is on an upper support plate of the scissor-type arm on which the scissor-type arm with both scissor halves is rotatably mounted. Since both scissor halves are moved uniformly on the scissor-type arm, the support plate remains in the horizontal position at all times, for example, the support plate is not displaced. The radiation detector also remains in a set position since it is connected to the upper support plate.

In one embodiment, the X-ray device includes an articulated arm. The radiation detector is rotatably mounted by a support on the upper arm of the articulated arm, with the swivel joint by which the support is rotatably mounted being movably coupled via a possibly additional mechanical coupling to the swivel joint by which the two arms are rotatably mounted. Via said rotatable mounting of the support and the provided mechanical movement coupling between the two swivel joints or the respective shafts of the swivel joints, the swiveling movement of the upper arm which with a rigid arrangement of the radiation detector on this arm would lead to a corresponding swiveling or tilting displacement of the radiation detector is advantageously compensated by way of a corresponding countermovement of the rotatably mounted supports. The mechanical movement coupling is configured such that the angular displacement of the arm of the articulated arm is fully compensated by an opposite-directed angular displacement of the support. The radiation detector remains in the set home position, for example, in the vertical position.

The mechanical coupling is a chain or belt drive, with the sprocket wheels or belt pulleys being arranged on the corresponding articulated shafts of the swivel joints. While the upper articulated shaft is non-rotatably connected to the support, the lower articulated shaft, which connects both arms, is non-rotatably connected to the upper arm.

In one embodiment, a radiation detector may be displaceably mounted between a vertical position and a horizontal position. This offers the possibility in the individual case not only to produce horizontal images, whereby the radiation detector is arranged in the vertical position, but also vertical images, whereby the radiation detector is positioned horizontally. This also offers the possibility, in connection with the embodiment of the inventive X-ray device having a scissor-type or articulated arm, to move the X-ray detector into a small-format position close to the floor and then move a patient examination table on which the patient to be examined is situated, over the X-ray device. The X-ray source is located above the table and the patient such that it radiates vertically downward in the direction of the horizontally aligned radiation detector located under the table.

The radiation detector may be tiltable by a drive device, for example, a drive motor, though hydraulic or pneumatic drives are also conceivable. For the purpose of controlling the swivel drive, a suitable control and operating device is provided, for example again in the form of a joystick which has to be moved to the left or right for a detector swiveling movement, for example, while it has to be moved forward and back for an upward and downward movement of the scissor-type or articulated arm. Alternatively, corresponding keys are possible, each of which is assigned to the corresponding detector tilt direction.

Alternatively to the automatic swiveling capability, the radiation detector can be swivelable manually, with at least the vertical position and the horizontal position being latched as defined swivel positions. The user may set the corresponding horizontal or vertical position in a simple manner.

In addition to the X-ray detector the invention also relates to an X-ray device, comprising an X-ray source and an X-ray detector of the type described.

BRIEF DESCRIPTION OF THE DRAWINGS

Further advantages, features and details of the invention will emerge from the exemplary embodiments described below as well as with reference to the drawings, in which:

FIG. 1 is a schematic diagram showing an X-ray detector having a scissor-type arm in an extended position, FIG. 2 shows the X-ray detector from FIG. 1 in a parked position.

DETAILED DESCRIPTION

Figure 3:
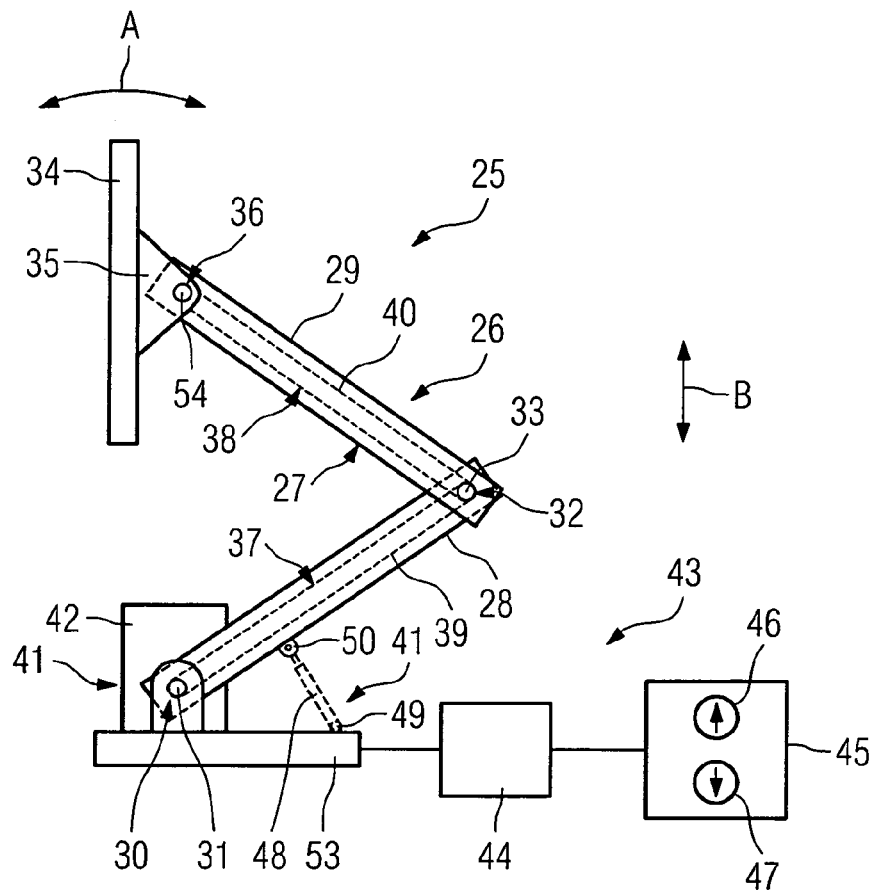
FIG. 3 is a schematic diagram showing a second X-ray detector having an articulated arm in a first position.

FIG. 1 shows an X-ray detector 1. The X-ray detector 1 includes a radiation detector 2, such as a solid-state detector, and a displacement mechanism 3, such as a scissor-type arm 4. The scissor-type arm 4 includes a plurality of separate struts 5, which are interconnected in a swivelable manner relative to one another at their ends and in a crossing point via swivel joints 6. The bottommost and topmost struts 5 are connected in a swivelable manner via separate swivel joints 7, 8 to a baseplate 9 and a top support plate 10, where they are horizontally movable, for the vertical displacement. The radiation detector 2 is arranged via a mount 11 on the support plate 10, such that the radiation detector 2 swivels around a further swivel joint 12, as indicated by the double arrow A. The scissor-type arm 4 is movable vertically, as indicated by the double arrow B, folding down or extending as applicable.

To allow a vertical movement of the scissor-type arm 4, whether for shortening or lengthening, a drive device 13, for example, a drive motor 14, is provided which engages in one of the two bottommost swivel joints 7. The drive motor 14 may be connected directly to the articulated shaft or the joint pin, which for its part is non-rotatably connected to the scissors 5a. If the articulated shaft 15 is rotated via the drive motor 14, the strut 5a is automatically swiveled via the drive motor 14 to the right or left. Because the strut 5a is coupled to adjacent struts 5 and the struts 5 are coupled to one another, this causes a vertical movement of the entire scissor-type arm 3. The radiation detector 2 may be moved up and down by the vertical movement.

A control or operating device 16, in this case in the form of a control unit 17 and a joystick 18, is provided for the purpose of controlling the movement. The joystick may be pushed forward and back, for example, as indicated by the two arrows a and b. Corresponding rotational directions of the drive motor 14, and consequently movement directions of the scissor-type arm 4, are assigned to the two directions. When the joystick is moved in the direction of the arrow a, for example, when the joystick is pushed back, the scissor-type arm extends, and when the joystick is pulled in the direction of the arrow b, the arm folds down.

As described, the radiation detector 2 is also swivelable about the rotation axis 12. The radiation detector 2 may be manually swiveable, wherein the defined vertical position and an assumable horizontal position can be latched, for example. A drive device 19, for example, a drive motor 20, acts directly on the swivel joint 12 or the articulated shaft 21. The detector swivel movement may be controlled via the joystick 18 which for this purpose can be moved in two further directions, as indicated by the arrows c and d. The movement directions are normal relative to the directions according to the arrows a, b. Each movement direction is in turn assigned to a corresponding swivel direction. If the detector is to be moved, for example, from the vertical position, as shown in FIG. 1, into a horizontal position, the joystick is pushed, for example, in the direction of the arrow c until the vertical position has been assumed. The resetting movement is effected by moving the joystick 18 in the direction of the arrow d A single short tapping of the joystick 18 in the respective direction c, d may enable a full displacement between horizontal and vertical position, the displacement movement being automatically limited when the respective end position has been assumed.

FIG. 2 shows the X-ray detector 1 from FIG. 1 in a closed, small-format position. The scissor-type arm 4 may be folded down, effected as a result of corresponding control of the drive motor 14. The drive motor 20 has been controlled accordingly in order to move the detector 2 into a horizontal position. As shown in FIG. 2, a patient examination table 22 may be moved over the radiation detector 2. The X-ray source 23 is situated above the table with the examination object 24 so that vertical images can be taken. The X-ray detector 1 may be arranged in a freestanding manner in the room without the use of correspondingly high guide rods and some other elaborate movement-mimicking system, as well as the fact that this can be closed into a very small format, allows a potential new application also of such a grid wall device than, as described, being able to be moved over by a patient examination table for the purpose of taking vertical images. The X-ray detector 1 and the radiation source 23, which is preferably ceiling-mounted by a stand, form an X-ray device, wherein the patient examination table 22 can be part of the same, but does not necessarily have to be.

Figure 4:
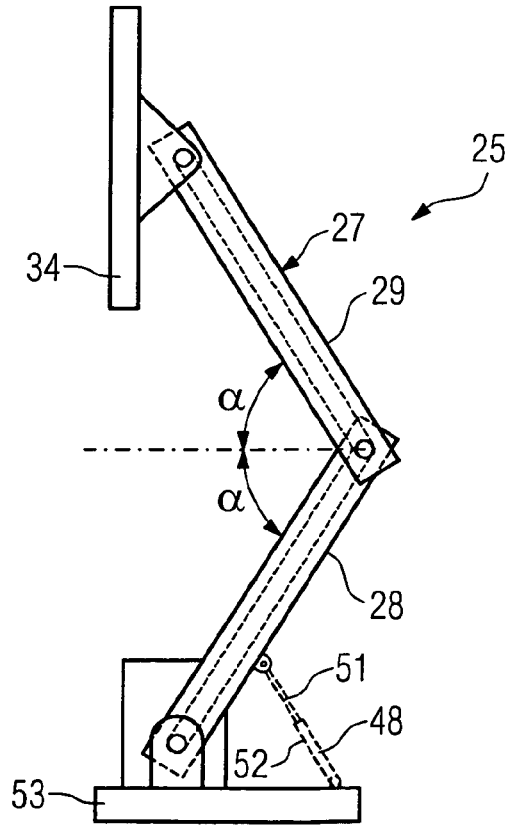
FIG. 4 shows the X-ray detector from FIG. 3 in a further extended position.

In one embodiment, as shown in FIGS. 3 and 4, the X-ray detector 25 includes a movement device 26 in the form of an articulated arm 27, which includes a lower arm 28 and an upper arm 29. The lower arm 28 is disposed on a baseplate 53 and swivelably mounted via a swivel joint 30 with an articulated shaft 31. A further swivel joint 32 with an articulated shaft 33 joins the two arms 28, 29, the arm 29 is non-rotatably connected to the rotational axis 33. The radiation detector 34 is swivelably mounted via a support 35 at the free end of the arm 29 in a swivel joint 36 including an articulated shaft 54. The support 35 is non-rotatably connected to the articulated shaft 54.

To allow simultaneous movement of both arms 28, 29 and to ensure that the radiation detector 34 is not moved out of its set position during a movement of the articulated arm 27, two mechanical movement couplings 37, 38 are provided which are each embodied as chain or belt drives 39, 40. Viewed in cross-section, the arms 28, 29 are square or rectangular, but may be hollow. Accordingly, the chain or belt drives 39, 40 may be integrated into the arms 28, 29. Sprocket wheels or disk pulleys, around which runs the respective chain or belt of the respective chain or belt drive 39, 40, may be arranged on bearing shafts 31, 33, and 54. The bearing shaft 31 is non-rotatably connected to the arm 28 such that a rotary movement of the bearing shaft 31 initiated via the drive device 41. A drive motor 42 may interact directly with the bearing shaft 31, which leads to a swivel movement of the arm 28. During the rotation of the bearing shaft 31 the sprocket wheel or belt pulley may be rotated, thereby moving the chain or belt. This movement is transmitted to the bearing shaft 33, which is non-rotatably connected to the arm 29. A movement of the arm 29 is initiated which by suitable implementation of the transmission ratio is moved by the same angle as the arm 28.

Due to the movement coupling 38, the radiation detector 34 remains in the assumed position. If the arm 29 is moved as a result of a rotation of the bearing shaft 33 the chain or belt of the chain or belt drive 40 is also necessarily moved. The movement is transmitted to the bearing shaft 54, which is connected to the support 35. The movement coupling 38 is configured such that the support 35 is moved by the same angular increment in the opposite direction as the arm 29 in order to compensate for the angular displacement and hold the radiation detector 34 in the assumed original position. The movement couplings 37, 38 in the form of the chain or belt drives 39, 40 are simply schematic representations. The movement couplings are implemented in such a way as to produce the desired uniform movement of the two arms 28, 29 and the corresponding displacement compensation at the support 35 in order to maintain the detector position.

The control of the movement of the articulated arm 26 which, as the arrow B shows, can also be displaced vertically in both directions is effected via a control and operating device 43. The control and operating device 43 includes a control unit 44 and, for example, a key panel 45. The key panel 45 has a first key 46, which as indicated by the arrow serves for extending the articulated arm 27. The key 47 serves to fold down the articulated arm 27, as indicated by the corresponding direction arrow.

The radiation detector 34 may be tilted, as indicated by the arrow A. The radiation detector 34 may be swiveled between a defined vertical position, which is shown in FIG. 3, and a defined horizontal position. In this case a manual swiveling capability is provided. The vertical position, as shown in FIG. 3, and the horizontal position are latched, for example, so that the user when tilting the radiation detector 34 senses when he has reached the desired end position. It would of course be conceivable to provide a corresponding drive motor.

FIG. 4 shows the X-ray detector 25 in a further extended position. Owing to the movement coupling between the two arms 28, 29 the angle that both assume relative to the horizontal in the area of the smaller, inner arm angle is the same. The inner arm angle is specified by a. Since both arms are moved uniformly, the angle α is always the same irrespective of the actual extension or parking position of the articulated arm 27. As FIG. 4 shows, the vertical position of the radiation detector 34 has not changed in spite of the articulated arm 27 being extended.

As FIGS. 3 and 4 also show, a different drive device 41 may be used, instead of a drive motor 42. The second drive device 41 shown here only by a dashed outline is implemented as a hydraulic or pneumatic cylinder 48, which can be controlled in a corresponding manner via the control and operating device 43. It is arranged with its lower end on a swivel joint 49 on the baseplate 53, while the upper end is hinged to the lower arm 28 via a corresponding swivel joint 50. In order to adjust the articulated arm 27 the piston 51 is driven out of or moved into the piston housing 52. The lower articulated arm 28 may be swiveled about the swivel joint 30 and the entire articulated arm 27 is lengthened or shortened.

Although not shown in more detail here, it is also possible to fold down the X-ray detector 25 to such an extent that a patient examination table 22 (not shown in further detail) together with patient can then be moved over the radiation detector 34, then positioned horizontally, and vertical images can be taken.

The invention claimed is:

1. An X-ray detector that is a grid wall device, the X-ray detector comprising:
a radiation detector that is movable vertically by a displacement mechanism,
wherein the displacement mechanism includes:
a scissor arm or an articulated arm having at least two arms hinged together; and
at least one drive device that is operable to automatically move the scissor arm or the articulated arm, and
wherein the radiation detector is arranged on the scissor arm or the articulated arm such that the radiation detector does not change position relative to a vertical during a movement of the scissor arm or the articulated arm.

2. The X-ray detector as claimed in claim 1, wherein the at least one drive device is a drive motor, a hydraulic cylinder, or a pneumatic cylinder.

3. The X-ray detector as claimed in claim 1, wherein the at least one drive device engages directly on or in a swivel joint of the scissor arm or the articulated arm.

4. The X-ray detector as claimed in claim 2, wherein the displacement mechanism includes the articulated arm, and
wherein the at least two arms of the articulated arm are movably coupled by a mechanical coupling.

5. The X-ray detector as claimed in claim 4, wherein the mechanical coupling is a chain or belt drive.

6. The X-ray detector as claimed in claim 4, wherein the mechanical coupling is arranged in an interior of a lower arm of the at least two arms and extends between a lower swivel joint and a swivel joint connecting the at least two arms.

7. The X-ray detector as claimed in claim 1, wherein the displacement mechanism includes the scissor arm, and
wherein the radiation detector is arranged on an upper support plate of the scissor arm, the upper support plate being rotatably mounted with scissor halves.

8. The X-ray detector as claimed in claim 1, wherein the displacement mechanism includes the articulated arm, and
wherein the radiation detector is arranged rotatably mounted via a support on an upper arm of the articulated arm, a first swivel joint, via which the support is rotatably mounted, being movably coupled via a mechanical coupling to a second swivel joint, via which the at least two arms are rotatably mounted.

9. The X-ray detector as claimed in claim 8, wherein the mechanical coupling is a chain or a belt drive.

10. The X-ray detector as claimed in claim 8, wherein the mechanical coupling is arranged in an interior of the upper arm and extends between the second swivel joint and the first swivel joint.

11. The X-ray detector as claimed in claim 1, wherein the radiation detector is operable to be swiveled between a vertical position and a horizontal position.

12. The X-ray detector as claimed in claim 11, wherein the radiation detector is operable to be swiveled by a drive device.

13. The X-ray detector as claimed in claim 12, wherein the drive device is a drive motor.

14. The X-ray detector as claimed in claim 11, wherein the radiation detector is operable to be swiveled manually, and
wherein at least the vertical position and the horizontal position are latched as defined swivel positions.

15. An X-ray system comprising:
an X-ray source that is operable to generate an x-ray beam; and
an X-ray detector that is operable to detect the x-ray beam, wherein the X-ray detector comprises a radiation detector that is movable vertically by a displacement mechanism, the displacement mechanism including a scissor arm or an articulated arm having at least two arms hinged together, and at least one drive device that is operable to automatically move the scissor arm or the articulated arm, and
wherein the radiation detector is arranged on the scissor arm or the articulated arm such that the radiation detector does not change position relative to a vertical during a movement of the scissor arm or the articulated arm.

16. The X-ray detector as claimed in claim 3, wherein the at least one drive device engages directly on a bottom swivel joint located adjacent to a floor-side mounting of the scissor arm or the articulated arm.

17. The X-ray detector as claimed in claim 5, wherein the chain or belt drive is arranged in an interior of a lower arm of the articulated arm and extends between a lower swivel joint and a swivel joint connecting the at least two arms.

18. The X-ray detector as claimed in claim 8, wherein a chain or belt drive is arranged in an interior of the upper arm and extends between the second swivel joint and the first swivel joint.

* * * * *